US006673081B1

(12) United States Patent
Tavger et al.

(10) Patent No.: US 6,673,081 B1
(45) **Date of Patent: *Jan. 6, 2004**

(54) DERMAL ABRASION

(75) Inventors: Michael Tavger, Katzrin (IL); Ella Lindenbaum, Haifa (IL)

(73) Assignee: Tav Tech Ltd., Katzrin (IL)

( * ) Notice: Subject to any disclaimer, the term of this patent is extended or adjusted under 35 U.S.C. 154(b) by 0 days.

This patent is subject to a terminal disclaimer.

(21) Appl. No.: 09/529,844

(22) PCT Filed: Oct. 22, 1998

(86) PCT No.: PCT/IL98/00517

§ 371 (c)(1),
(2), (4) Date: Apr. 20, 2000

(87) PCT Pub. No.: WO99/20336

PCT Pub. Date: Apr. 29, 1999

(30) Foreign Application Priority Data

Oct. 22, 1997 (IL) ................................................ 122016

(51) Int. Cl.[7] ........................ A61B 17/50; A61M 35/00; A61M 37/00

(52) U.S. Cl. ....................... 606/131; 604/289; 604/290; 604/24

(58) Field of Search ................................ 604/289, 290, 604/24, 140; 606/131; 433/88–89

(56) References Cited

U.S. PATENT DOCUMENTS

| | | | | | |
|---|---|---|---|---|---|
| 28,405 | A | * | 5/1860 | Sollerud | 417/545 |
| 3,574,239 | A | | 4/1971 | Sollerud | |
| RE28,405 | E | | 5/1975 | Sollerud | |
| 4,646,480 | A | * | 3/1987 | Williams | 451/102 |
| 5,152,435 | A | | 10/1992 | Stand et al. | |
| 5,295,982 | A | * | 3/1994 | Schatz | 604/313 |
| 5,447,504 | A | * | 9/1995 | Baker et al. | 601/166 |
| 5,620,414 | A | * | 4/1997 | Campbell, Jr. | 604/150 |
| 5,630,793 | A | | 5/1997 | Rowe | |
| 5,810,842 | A | * | 9/1998 | Di Fiore et al. | 606/131 |
| 5,843,052 | A | * | 12/1998 | Benja-Athon | 604/289 |
| 6,283,936 | B1 | * | 9/2001 | Tavger | 604/24 |

OTHER PUBLICATIONS

H. Murad, et al., “The use of glycolic acid as a peeling agent”, Apr. 1995, Dermatologic Clinics 13(2):285–307.(Abstract).

M. G. Rubin, “A peeler’s thoughts on skin improvement with chemical peels and laser resurfacing”, Apr. 1997, Clinics in Plastic Surgery 24(2):407–9.(Abstract).

* cited by examiner

*Primary Examiner*—Dennis Ruhl
*Assistant Examiner*—Linh Truong
(74) *Attorney, Agent, or Firm*—Pearne & Gordon LLP

(57) ABSTRACT

The present invention is a method of dermal abrasion, that includes exposing a source of sterile liquid to a flow of pressurized gas, thereby causing a pumped supply thereof into a fluid delivery head (200); supplying the pressurized gas to the fluid delivery head; combining the gas, and liquid (204) supplied to the delivery head; this fluid delivery head having a fluid outlet (206) with a predetermined internal diameter (210), so as to provide a gas-liquid outflow in the form of a sterile liquid mist jet suspended in a high velocity gas stream; and exposing to the mist jet, at a preselected distance from the fluid outlet, a portion of the skin surface (224) sought to be abraded, thereby separating therefrom at least a portion of the epidermis (225), and removing therefrom the resulting tissue debris.

24 Claims, 7 Drawing Sheets

Figure 1:
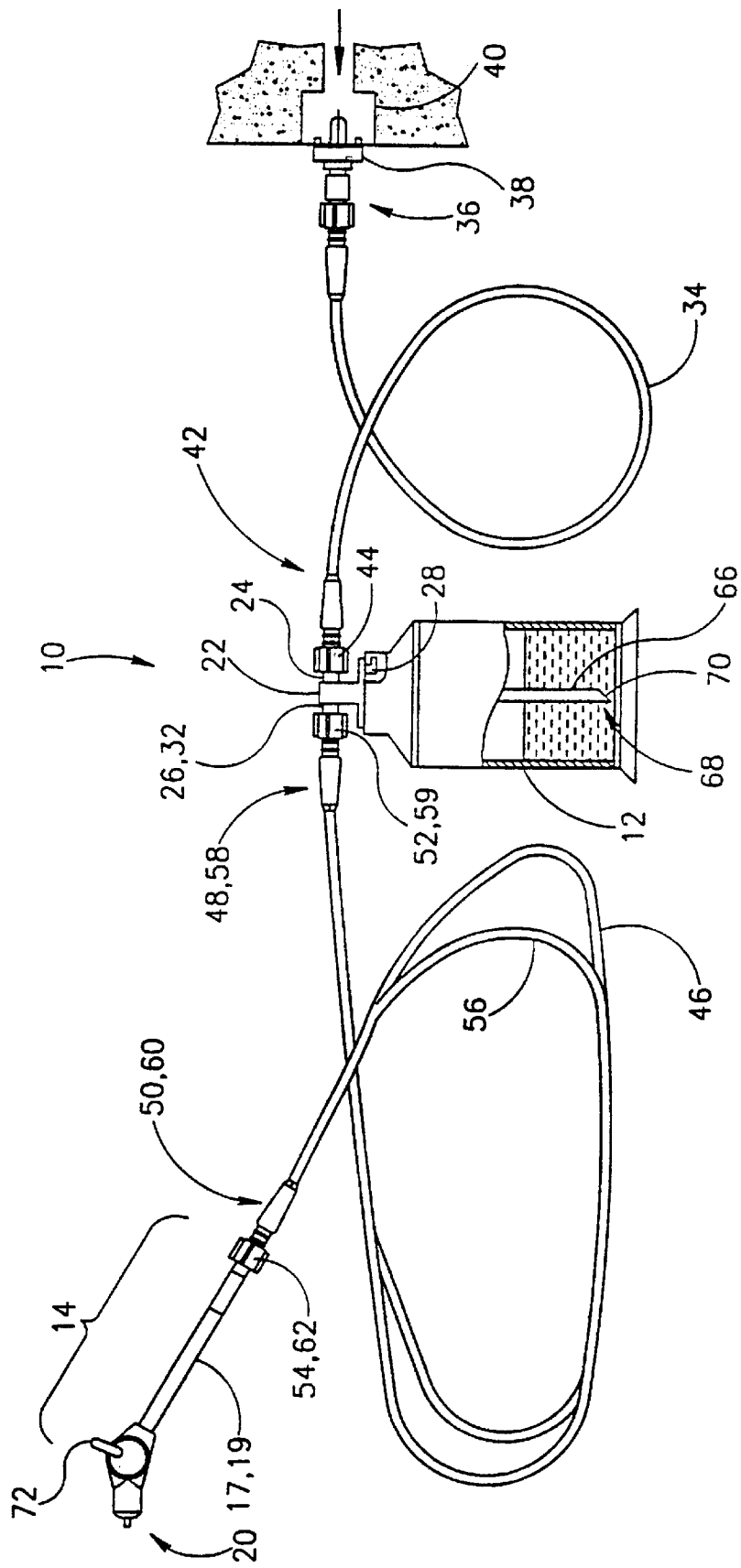

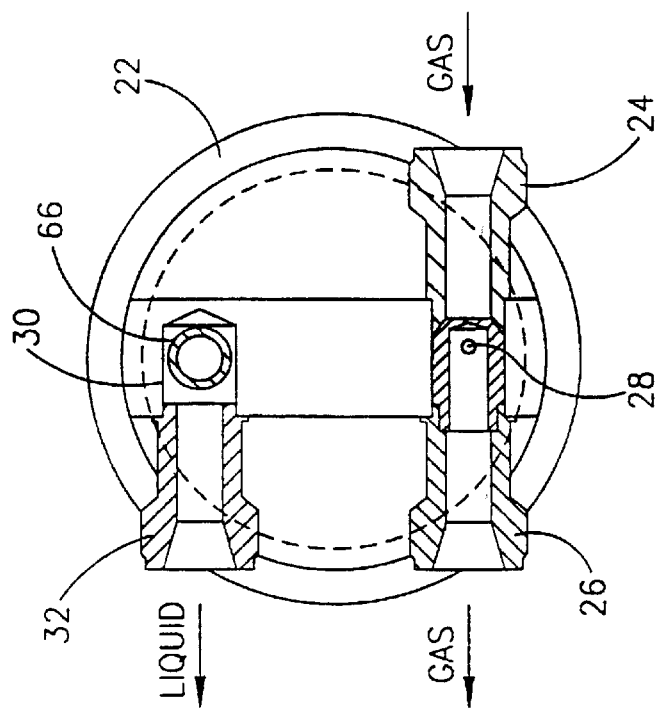
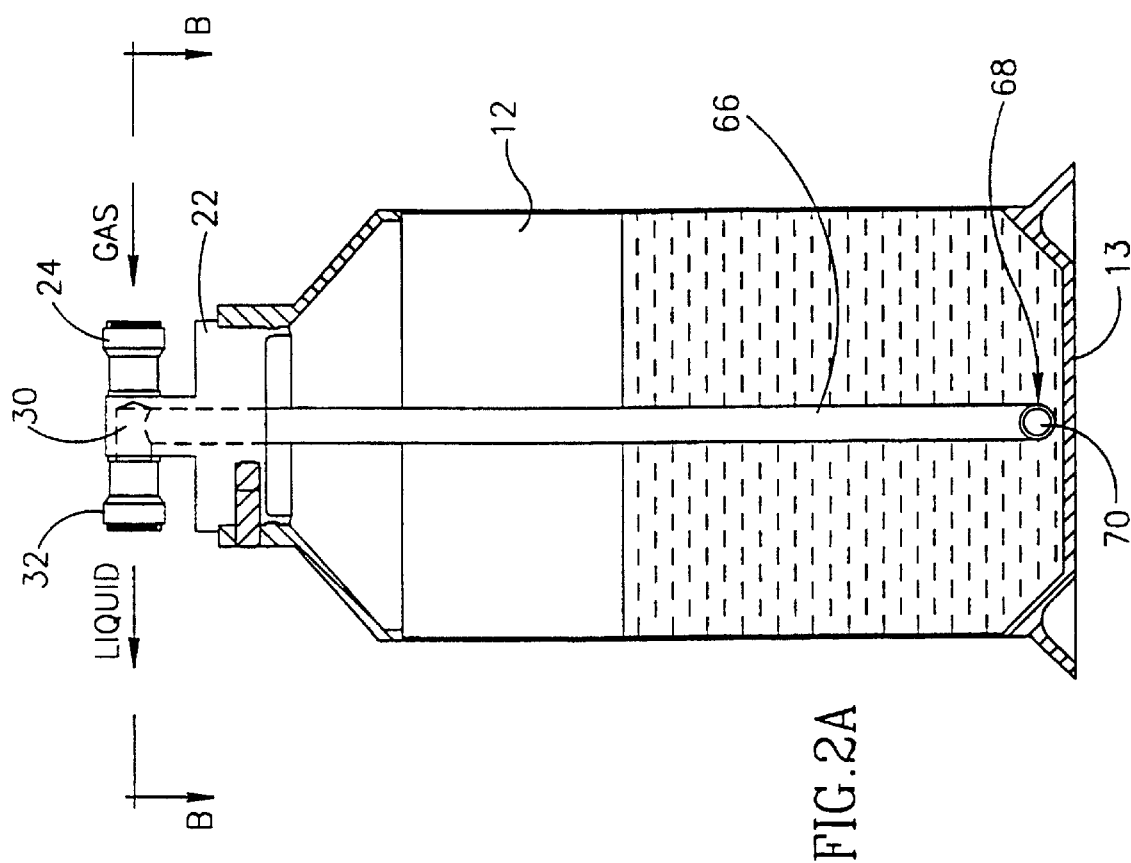
FIG.2B
FIG.2A

DERMAL ABRASION

FIELD OF THE INVENTION

The present invention relates to cosmetic surgery in general; and, to dermal abrasion, in particular.

BACKGROUND OF THE INVENTION

The peeling of skin from the human body is well known for cosmetic purposes. While it is particularly well known in the context of facial cosmetic surgery, for the peeling of aging, wrinkled, or otherwise blemished skin, it is also known for the peeling of skin from other parts of the body, such as from the feet.

Among known methods of cosmetic skin peeling are dermal abrasion, and chemical peeling. Known dermal abrasion techniques include either the use of various mechanical methods so as to remove unwanted skin; or the use of irradiation treatments of various types, including the employment of laser surgical techniques. Chemical peeling involves the application of a film-forming chemical substance to the skin sought to be peeled, and subsequently removal of the film together with an outer layer of the epidermis. See, for example, the review article "The use of glycolic acid as a peeling agent" by Murad, Shamban, and Premo in Dermatologic Clinics 13(2), 1995.

The above-mentioned methods are characterized by various disadvantages, including recuperative periods which can last from several days to several months. Known methods of dermal abrasion, furthermore, can be very painful and cause a large amount of bleeding while being performed. The use of laser methods, moreover, requires very expensive equipment, consuming large amounts of energy; which, if improperly used, can cause severe burn damage to a patient. Many of these problems and limitations are reviewed in "A peelers thoughts on skin improvement with chemical peels and laser resurfacing" by M. G. Rubin in Clinics in Plastic Surgery 24(2) 1997.

Furthermore, the above methods generally require performance by and the supervision of skilled medical personnel, and cannot generally be performed by users in a domestic environment.

SUMMARY OF THE INVENTION

The present invention seeks to provide a novel apparatus and method of dermal abrasion, which overcome disadvantages of the known art.

There is thus provided, in accordance with a preferred embodiment of the invention, apparatus for dermal abrasion, which includes:

a container for a sterile liquid;

a fluid delivery head having a liquid entry port and a gas entry port, a fluid outlet, and a valve located between the entry ports and the fluid outlet, for selectably permitting respective liquid and gas flows from the entry ports to the fluid outlet;

a liquid conduit extending between a liquid inlet located within the container and a liquid outlet connected to the liquid entry port of the delivery head;

a gas conduit extending between a gas inlet and a gas outlet, wherein the gas inlet is connected to a source of pressurized gas and the gas outlet is connected to the gas entry port of the delivery head, and wherein the gas conduit is connected to the container via an intermediate outlet port; and apparatus for selectably exposing the source of sterile liquid to a flow of pressurized gas flowing from the gas inlet to the gas outlet and into the gas entry port of the fluid delivery head, thereby to pump the sterile liquid along the liquid conduit, from the inlet to the outlet, and into the liquid entry port of the fluid delivery head, and apparatus wherein the fluid outlet has one or more nozzle members arranged to receive the gas and liquid flows and to combine them into a corresponding number of gas-liquid outflows which exit the apparatus through the fluid outlet in the form of sterile liquid mist jets suspended in a high velocity gas stream, and wherein the jets are operative, when brought to within a preselected distance from the skin surface to be abraded, to separate therefrom at least a portion of the epidermis.

Additionally in accordance with a preferred embodiment of the present invention, the gas flow exits the valve into the gas-liquid combining member at a pressure of a first magnitude, and the combining member is operative to cause a pressure drop in the gas flow therethrough such that the pressure of the gas-liquid outflow downstream of the fluid outlet, is of a second magnitude, wherein the first magnitude is at least twice the second magnitude, so as to cause a shock wave in the gas-liquid flow downstream of the fluid outlet and atomizing of the liquid portion of the outflow into microscopic droplets, thereby to form a mist suspended in the gas portion of the outflow.

Further in accordance with a preferred embodiment of the present invention, at least a portion of the gas-liquid outflow downstream of the fluid outlet, has a sonic or supersonic velocity.

Additionally in accordance with a preferred embodiment of the present invention, the gas inlet of the gas conduit is constructed for connection to a pressurized gas source, and the outflow is an outflow of the sterile liquid mist suspended in a high velocity gas stream.

Further in accordance with a preferred embodiment of the present invention, the fluid outlet is configured so as to apply a suction force in the vicinity of the skin surface being abraded so as to remove tissue debris therefrom.

Additionally in accordance with a preferred embodiment of the present invention, the fluid outlet defines a fluid outlet port having a predetermined diameter and a preselected distance of operation; that is, the distance between the skin being abraded and the nearest portion of the delivery head to the skin being treated; wherein this distance of operation is not greater than 50 times and preferably within a range of 1–5 times the predetermined diameter.

Further in accordance with alternative embodiments of the present invention, the sterile liquid optionally contains predetermined amounts of crystalline or other microscopic particles to increase its abrasive properties, or of chemicals which cause peeling of the outer skin layers.

There is also provided, in accordance with a further preferred embodiment of the invention, a method of dermal abrasion, which includes:

- exposing a source of sterile liquid to a flow of pressurized gas, thereby to cause a pumped supply thereof into a fluid delivery head;
- supplying the pressurized gas to the fluid delivery head;
- combining the gas and liquid supplied to the delivery head, wherein the fluid delivery head has a fluid outlet with a predetermined internal diameter, so as to provide a gas-liquid outflow in the form of a sterile liquid mist jet suspended in a high velocity gas stream; and
- exposing to the mist jet, at a preselected distance from the fluid outlet, a portion of the skin surface sought to be abraded, thereby separating therefrom at least a portion of the epidermis and removing therefrom the resulting tissue debris.

Further in accordance with a preferred embodiment of the present invention, the preselected distance is not greater than 50 times and preferably within a range of 1–5 times the predetermined internal diameter.

Additionally in accordance with the method of the invention, the step of supplying the pressurized gas includes supplying the gas at a pressure of a first magnitude, and the step of combining includes causing a pressure drop in the gas flow such that the pressure of the gas-liquid outflow, is of a second magnitude, wherein the first magnitude is at least twice the second magnitude, so as to cause a shock wave in the gas-liquid outflow and atomizing of the liquid portion of the outflow into microscopic droplets, thereby to form a mist suspended in the gas portion of the outflow.

Preferably, at least a portion of the outflow has either a sonic or supersonic velocity.

Further in accordance with a preferred embodiment of the present invention, the method also includes the steps, prior to the step of combining, of providing a gas outflow;

causing an expansion of the gas outflow, thereby to cause a reduction in the pressure thereof to sub-atmospheric pressure, thereby to provide a suction force; and providing a liquid outflow in conjunction with the expanded gas outflow.

BRIEF DESCRIPTION OF THE DRAWINGS

The present invention will be more easily understood and appreciated from the following detailed description, taken in conjunction with the drawings, in which:

FIG. 1 is a general view of a novel dermal abrasion apparatus, constructed in accordance with a preferred embodiment of the present invention;

FIG. 2A is an enlarged, part-sectional side view of the container seen in FIG. 1;

FIG. 2B is an enlarged cross-sectional view of the distributor cap of the container of FIG. 2A, taken along line B—B therein;

FIG. 3A is a detailed cross-sectional view of the fluid delivery head seen in FIG. 1, when in use;

FIG. 3B is an enlarged detailed illustration of a portion of the valve mechanisms, in open positions;

FIG. 3C is an enlarged detailed illustration of a portion of the valve mechanisms, in closed positions;

FIGS. 4A–4C are diagrammatic illustrations showing successive stages in dermal abrasion in accordance with a preferred embodiment of the present invention;

FIG. 5 is a partial side view of a fluid delivery head constructed in accordance with an alternative embodiment of the invention, and having a nozzle portion which is configured to create a suction pressure in its immediate vicinity;

FIG. 6 is an enlarged diagrammatic side-sectional view of the nozzle of the fluid delivery head seen in FIG. 5, showing the formation of the suction pressure thereby;

FIG. 7 is a fragmentary schematic view of a multiple nozzle dermabrasion head formed in accordance with a preferred embodiment of the invention; and FIG. 8 is a bottom view of the head of FIG. 7, showing a nozzle array thereof.

DETAILED DESCRIPTION OF THE INVENTION

Referring now to FIG. 1, the present invention provides apparatus, referenced generally 10, which employs liquid and gas as working fluids for a novel method of dermal abrasion. Principal uses of the apparatus of the invention are for peeling of facial skin, and for the removal of skin on the feet, scar tissue, and various other surface blemishes on the skin.

It will be appreciated from the following description that the present apparatus is not only highly effective, but also, that it is inherently safe; it does not always require the presence of skilled medical personnel, and no concentrated energy sources are required.

Apparatus 10 includes a container 12 for containing a supply of a sterile liquid, such as any suitable saline solution, such as a 0.9% sodium chloride solution suitable for irrigation, and a fluid delivery head 14. Referring now also to FIG. 3A, head 14 has a liquid entry port 16, a gas entry port 18, and fluid outlet apparatus 20, via which a gas and liquid mist outflow is provided at a velocity which is either sonic or supersonic. It is this outflow which is used for dermal abrasion as described below.

By way of example, container 12 may be closed with a five-way distributor cap 22, which is fastened to the container as by use of a screw thread (not shown), or by a snap-type or other suitable coupling. Referring now also to FIGS. 2A and 2B, distributor cap 22 has a gas inlet port 24, first and second gas outlet ports, respectively referenced 26 and 28 (FIGS. 1 and 2B), a liquid inlet port 30, and a liquid outlet port 32.

A first gas conduit 34 (FIG. 1) has an inlet end 36, which is coupled in any suitable manner, as by connectors 38 and 40, to any suitable source of pressurized gas, preferably air, typically having an outlet pressure in the range 3–10 atmospheres. An air pressure in the lower portion of the range is useful for lighter dermal abrasion applications, such as from the face or other relatively sensitive parts of the body. Preferably, the gas supply has a generally steady, non-pulsating pressure head.

First gas conduit 34 also has an outlet end 42 which is attached, via a suitable screw or snap coupling 44, to gas inlet port 24. A second gas conduit, referenced 46, has an inlet end 48 and an outlet end 50. Inlet end 48 is attached, via a coupling 52, similar to coupling 44, to first gas outlet port 26, and outlet end 50 is attached, via suitable coupling 54, also similar to coupling 44, to an entry port 18' of a secondary gas conduit 19, coupled to gas entry port 18 of delivery head 14, as shown in FIG. 3A.

A liquid conduit 56 has an inlet end 58 which is attached, via a coupling 59, similar to coupling 44, to liquid outlet port 32 of distributor cap 22, and, further, has an outlet end 60 which is attached, as by a suitable coupling 62, also similar to coupling 44, to an entry port 16' of a secondary liquid conduit 17, coupled to liquid entry port 16 of delivery head 14, as shown in FIG. 3A.

A further tube portion, referenced 66, (FIGS. 1 and 2A) is attached to liquid inlet port 30 of distributor cap 22, and has a free end 68, extending towards the floor 13 of container 12, and which defines a liquid inlet 70.

As seen in FIGS. 2A and 2B, distributor cap 22 is formed such that gas inlet port 24 is connected with first and second gas outlet ports 26 and 28, thereby to facilitate a flow of gas from first gas conduit 34 (FIG. 1), through cap 22, and into second gas conduit 46 (FIG. 1), while also facilitating a pressurized supply of gas into container 12, via second gas outlet port 23. Liquid inlet port 30 and liquid outlet port 32 are also connected to each other, as seen, although the gas and liquid flows through the distributor cap 22 are kept separate.

It will thus be appreciated that, when gas flow through the first and second gas conduits 34 and 46 is permitted, by appropriate adjustment of thumb-operated levers 72 of delivery head 14 (described below), a portion of the pressurized air enters container 12 via second gas outlet port 28, thereby to pressurize the liquid in the container. This increase in pressure, coupled with a pressure difference between the interior of the container and the outlet apparatus 20 of the delivery head 14, causes an outflow of liquid from the container, into liquid inlet 70 of tube portion 66, into liquid exit port 32 and through cap 22, and thus also into liquid conduit 56. As will be appreciated from the description of FIGS. 3A–3C below, the pressure just downstream of fluid outlet apparatus 20 is atmospheric, thereby providing a required pressure drop, and thus enabling the described liquid outflow to occur. Preferably, levers 72 are linked by any suitable manner (not shown), so as to be operable simultaneously.

Figure 3A:
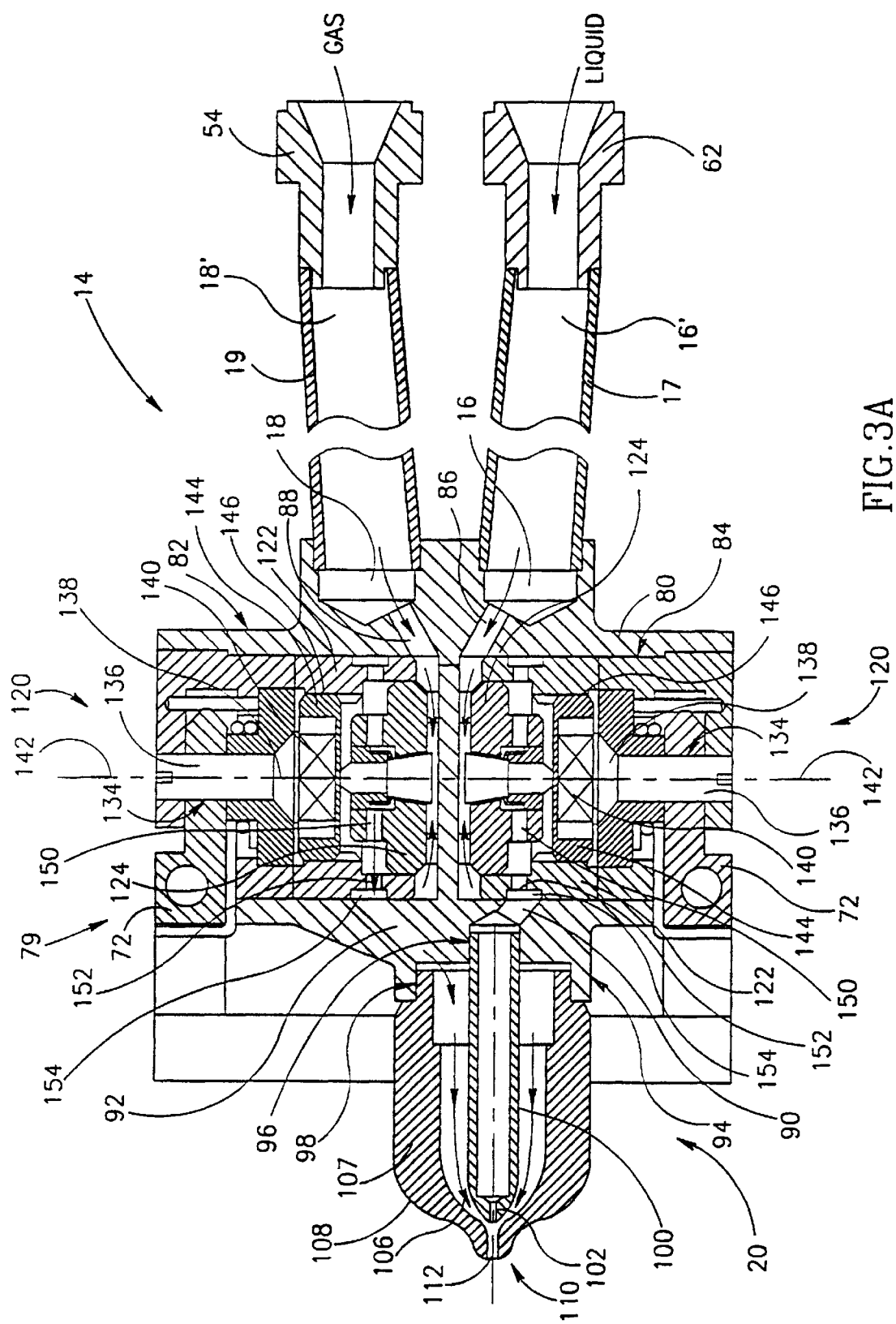
Figure 3B:
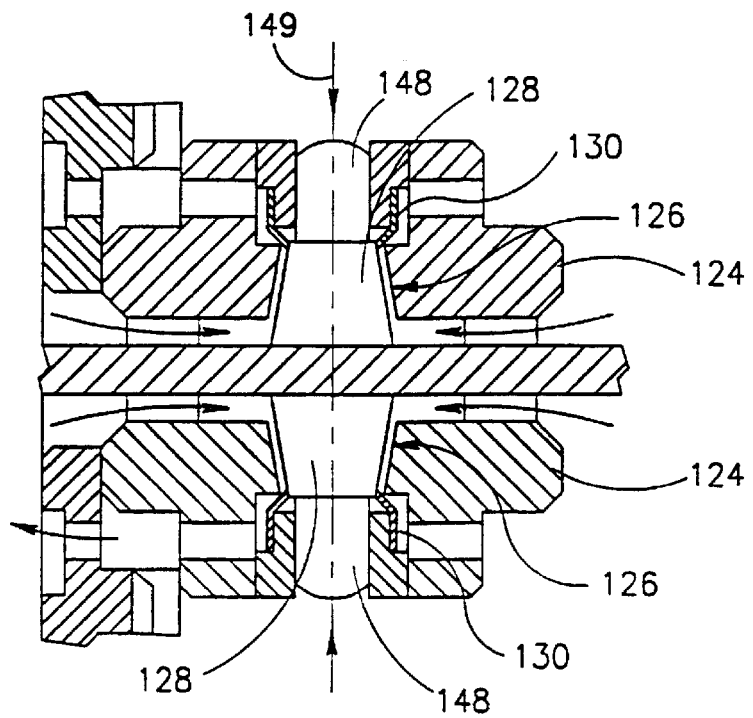
Figure 3C:
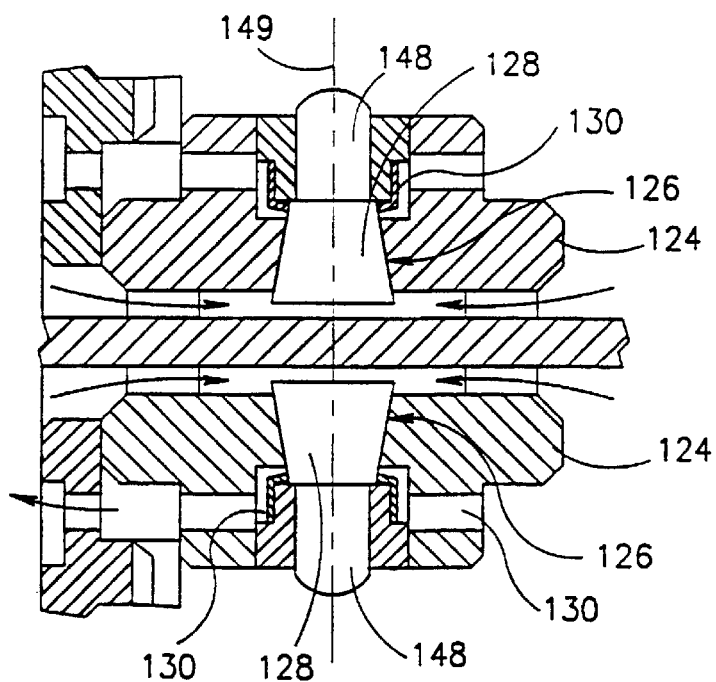

Reference is now made to FIGS. 3A, 3B and 3C, in which the fluid delivery head 14 (FIG. 3A) and portions of the valve mechanisms thereof (FIGS. 3B and 3C) are shown in detail. As described above, delivery head 14 has a liquid entry port 16, a gas entry port 18, and fluid outlet apparatus 20, via which a gas and liquid mist outflow is provided, at or exceeding, sonic velocity.

It will be appreciated by persons skilled in the art that the construction of the fluid delivery head 14, as described below in conjunction with FIGS. 3A–3C, is by way of example only, and other suitable types of connections and valves may be used, also in accordance with the invention.

Fluid delivery head 14 includes a valve assembly, referenced generally 79, which facilitates passage of liquid and gas, respectively, from liquid entry port 16 and gas entry port 18, to a gas and liquid combining nozzle member 108, described below. Valve construction 79 includes a body 80 which has formed, in a rear portion thereof, liquid entry port 16 and gas entry port 18. Body 80 further includes laterally positioned liquid and gas valve chambers, respectively referenced 82 and 84, and which are separated from each other, but which are connected with respective entry ports 16 and 18 via a first liquid supply bore 86 and a first gas supply bore 88. Valve chambers 82 and 84 are also connected, via respective second liquid supply bore 90 and second gas supply bore 92, to a front portion of body 80, referenced generally 94.

Front body portion 94 has formed thereon an inner recessed portion 96, and an outer recessed portion 98, which surrounds the inner recessed portion. Inner recessed portion 96 communicates with second liquid supply bore 90, and outer recessed portion communicates with second gas supply bore 92. An inner nozzle member 100 is seated within inner recessed portion 96 so as to be contiguous with second liquid supply bore 90, and terminates in a narrow bore front nozzle opening 102, through which a narrow jet of liquid is emitted. A cylindrical, gas-liquid combining member 108 is mounted within outer recessed portion 98 concentric with surrounding inner nozzle member 100.

Combining member 108 has a front portion, indicated generally 110, which is formed so as to converge towards an opening 112, which, as seen, is generally coaxial with nozzle opening 102 of inner nozzle member 100. Combining member 108 is configured so as to cause a central conversion of the gas throughflow in head 14 towards the liquid jet emerging from front nozzle opening 102. Accordingly, as the liquid jet and the gas flow converge upon each other, they become combined into a single gas and liquid jet in the front portion 110 of combining member 108.

Each of valve chambers 82 and 84 contains a valve mechanism, having a construction typically as described below. As these typical valve mechanisms are identical to each other, they are both indicated by reference numeral 120, and the components common to both valve mechanisms are indicated by similar reference numerals. Each valve mechanism 120 has a cylindrical seating member 122, in which is located an inner valve plate 124.

Referring now also to FIGS. 3B and 3C, it is seen that, in the present example, valve plate 124 has a generally conical, outwardly tapering valve opening 126 in which is seated a conical valve element 128. Valve element 128 is maintained, in the absence of any opposing forces, in a retracted, sealed position within opening 126, as shown in FIG. 3C, by resilient tension 130, such as a tension spring. Each thumb controlled lever 72 (FIGS. 1 and 3A) has a transversely extending threaded bore 134 (FIG. 3A) formed therein. As seen in FIG. 3A, a screw element 136 extends through bore 134 and terminates in a thickened end portion 138. A nut member 140 is connected to end portion 138, and is arranged for free rotation relative thereto, about the longitudinal axis 142 of screw element 136. Nut member 140 is seated in a piston-type casing 144 which is arranged for axial movement along inward-facing tracks 146 formed in seating member 122.

In the position shown in FIG. 3C, it is seen that valve opening 126 is closed by valve element 128. Rotation of lever 72 in a predetermined direction is operative to cause an inward linear translation of screw element 136. As nut member 140 is free to rotate about axis 142, it does not sustain any rotational moment, and is merely depressed inward by screw element 136. This inward movement causes a corresponding inward movement of casing 144 along tracks 146, which acts on a rear extension 148 of valve element 128 so as to depress it inwards, as shown by arrows 149 in FIG. 3B, thereby to cause a partial opening of valve opening 126, and enabling a throughflow of gas or liquid.

Valve plate 124 has a plurality of first radial bores 150 formed in a rear portion thereof, which communicate with the interior of valve seating member 122. Valve seating member 122 has one or more second radial bores 152, which communicate with an exterior recess 154.

The recesses 154 and the second liquid and gas supply bores 90 and 92 are formed such that opening of valve openings 126 (FIG. 36) enables respective throughflows of liquid and gas along flow paths constituted by valve openings 126, first radial bores 150 of valve plate 124, second radial bores 152 of valve seating member 122, recesses 154, and either of the supply bores 90 or 92.

As described above, the gas is pressurized, and is supplied at a steady pressure. While there may be a minimal head loss during flow through delivery head 14, the delivery head 14 is constructed so as to minimize such head loss, and so as to ensure that the fluid pressure remains—in even the 'lightest' applications—in excess of 2 atm, until the point where the combined jet emerges through opening 112 of combining member 108, into the atmosphere.

It will be appreciated by persons skilled in the art that, as the combined fluid jet emerges into atmospheric pressure, it undergoes an instantaneous pressure drop, from 2–10 atm or more, to 1 atm. A sudden pressure drop of this magnitude results in a velocity of the combined jet at the point of emergence into the atmosphere that approximates the velocity of sound, and in the production of a shock wave in the jet. The effect of the shock wave is to atomize the liquid fraction of the combined jet into microscopic water droplets, such that there is obtained a jet consisting of a liquid mist suspended in a gas jet, having a sonic or supersonic velocity.

Figure 4A:
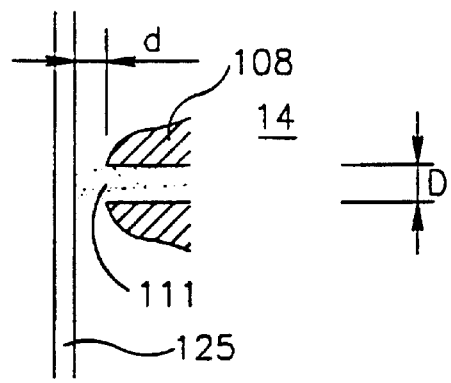
Figure 4B:
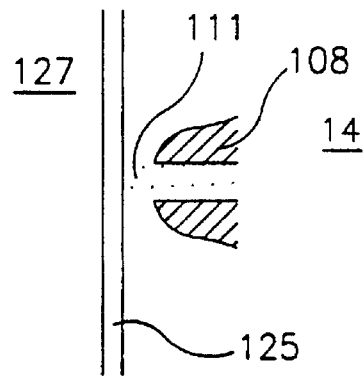

Referring now to FIGS. 4A–4B, a method of dermal abrasion is described, in accordance with a preferred embodiment of the present invention.

Figure 4C:
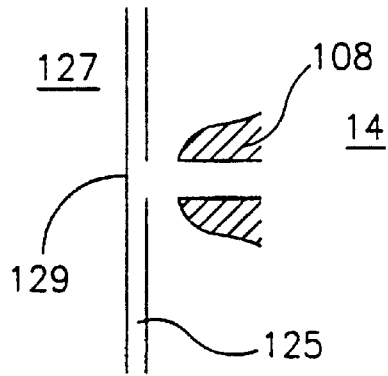

As seen in FIG. 4A, the delivery head 14 is held in close proximity to skin being abraded, at a distance 'd' which is predetermined to be suitable for the particular case at hand, and preferably, at a distance whereat the integrity of the jet is maintained. In all cases, distance 'd' is no greater than 50 times the narrowest dimension 'D' of the nozzle opening and preferably, is in the range 1–5 times the narrowest dimension 'D' of the nozzle opening. Typically, 'D' is in the range 1–3 mm. As seen, a mist jet 111 of microscopic liquid droplets bombards a targeted portion of the outermost layer of skin surface 125, thereby, after a predetermined time period, separating therefrom at least a portion of the epidermis. This is shown schematically in FIG. 4B. The tissue debris produced thereby continues to be bombarded and wetted by the mist jet 111, and is consequently washed from the remainder of the skin 127, such that a new layer of skin 129, behind the peeled layer, becomes exposed, as seen in FIG. 4C. The delivery head is moved gradually across the entire area from which the outer layer of skin is sought to be abraded.

By way of explanation, it will be appreciated that the above-descrbed wetting of the outer skin layer tissue debris in this way, namely, by microscopic droplets, causes a substantial increase in its aerodynamic resistance, such that the force of the bombardment by the combined fluid jet is able to separate it from the remaining skin surface, and to carry it away in the droplet stream. The increase in the aerodynamic resistance of the tissue debris is facilitated by the wetting by droplets, on the one hand, and by the absence of a liquid stream on the tissue surface with a stable boundary layer, on the other hand. Accordingly, as none of the separated layer is protected by a stable boundary layer of a liquid stream, it is all exposed to removal by the gas-liquid droplet stream.

It will further be appreciated that the pressure at which the device of the present invention is operated, and the length of time taken for abrading of skin from any particular area, depend, inter alia, on the nature of the skin (i.e. whether it is delicate facial skin, or calluses on the heel), and on the depth to which the skin is required to be abraded.

Figure 5:
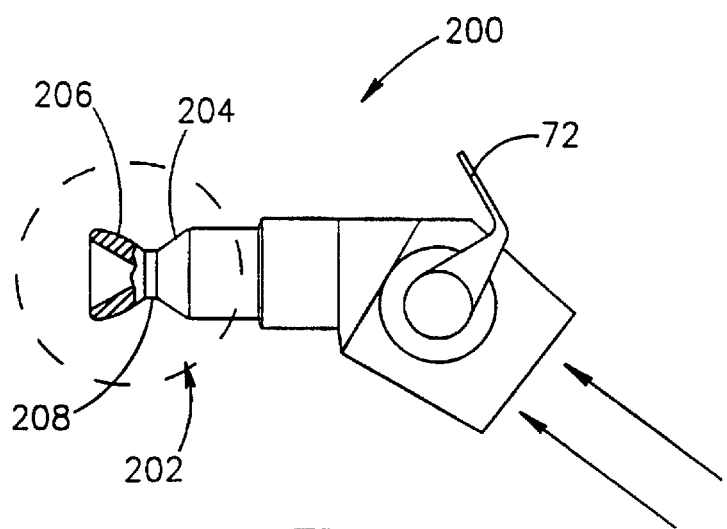
Figure 6:
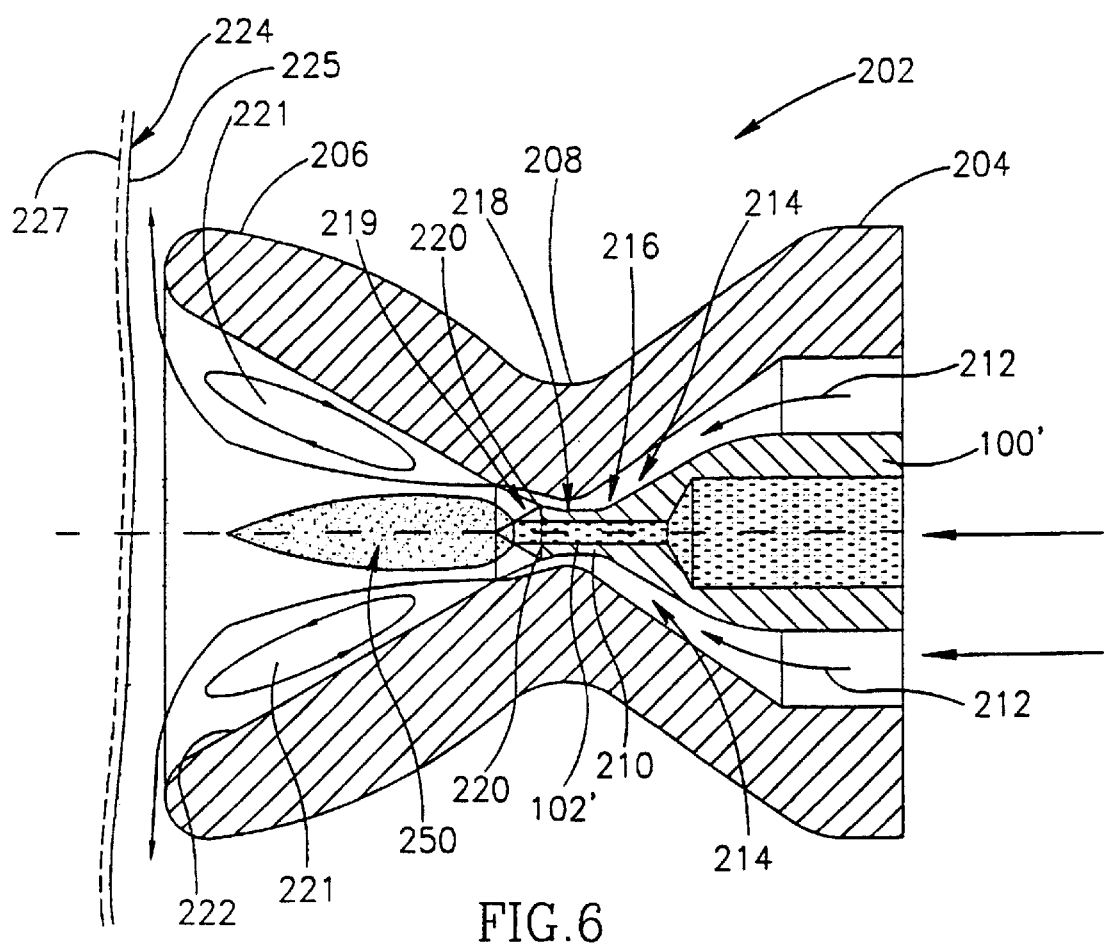

Reference is now made to FIG. 5, which illustrates a fluid delivery head, referenced generally 200, and to FIG. 6, which illustrates in detail the nozzle 202 of the fluid delivery head 200, constructed in accordance with an alternative embodiment of the invention. Delivery head 200 is similar to delivery head 14, shown and described above in conjunction with FIGS. 1 and 3A, and is thus not described again herein except with regard to differences between delivery head 200 and delivery head 14. Accordingly, components of delivery head 200 seen in either of FIG. 1 or 3A, and having counterpart components therein, are denoted in FIG. 6 by similar reference numerals but with the addition of a prime (') notation.

Referring again to FIG. 6, delivery head 200 is characterized by having a nozzle, referenced generally 202, which incorporates in a unitary member a rear, gas-liquid combining portion 204, and a front, suction portion 206. Nozzle 202 generally has an hourglass configuration, such that rear portion 204 and front portion 206 taper towards a narrow waist or transition portion 208. Inner nozzle member 100' is formed so as to protrude slightly through transition portion 208 and has a corresponding, slightly narrowed waist portion 210 whose diameter increases, as seen, as it protrudes into suction portion 206.

As an air stream, shown by arrow 212, at super-atmospheric pressure, enters the narrowing annular passageway 214, defined between inner nozzle member 100' and nozzle 202, it accelerates from a sub-sonic velocity, at the entrance 216 of the constricting passageway, to sonic velocity, at a location 218 part-way along the passageway, to supersonic velocity, at a location 219 defined by the abrupt termination of the constricted passageway, as the passageway opens out onto a step formed by front edge 220 of inner nozzle member 100'. As the gas flow emerges into the widening front nozzle portion 206 from transition zone 208, it expands rapidly. The expansion wave thus generated undergoes a considerable pressure drop, to at least sub-atmospheric pressure, thereby also giving rise to a conical rarefaction zone 221 along the inner surface 222 of front nozzle portion 206.

An accelerating liquid stream emerging through passing through nozzle opening 102' emerges into the supersonic gas stream, and, due to the sharp pressure drop experienced, substantially as described above in conjunction with FIGS. 1–3C, atomizes into microscopic droplets which are then swept into the gas stream, so as to form a combined gas-liquid mist stream at sonic or supersonic velocity. This combined stream is indicated generally by reference numeral 250.

When the fluid delivery head 200 is held in close proximity to skin 224 from which an outermost layer 225 is sought to be abraded, at a distance 'd' as described above in conjunction with FIG. 4A, part of epidermal layer 225 is exposed to the sonic or supersonic stream 250, so as to be separated from the remaining skin surface 227, as described above in conjunction with FIGS. 4A–4C. Subsequently, as head 200 is moved slowly across the skin surface, the tissue debris produced is exposed to the described sub-atmospheric pressure obtaining in the nozzle cavity, surrounding the stream 250.

It will thus be appreciated that, in addition to the microscopic liquid droplet bombardment as described above in conjunction with FIGS. 1–4C, the tissue debris is also exposed to a suction force as the nozzle is brought close to the skin, which further helps to remove the tissue debris from the remainder of the skin, prior to being carried away in the gas-liquid mist, thereby to leave a newly exposed-skin layer, referenced 227.

In an alternative embodiment of the present invention, the sterile liquid may include in suspension predetermined quantities of crystalline or other microscopic particles to increase its abrasive properties. In yet a further embodiment of the present invention, the sterile liquid may contain predetermined quantities of chemical substances known in the art to cause peeling of the outer skin layers, such as glycolic acid or TCA.

Figure 7:
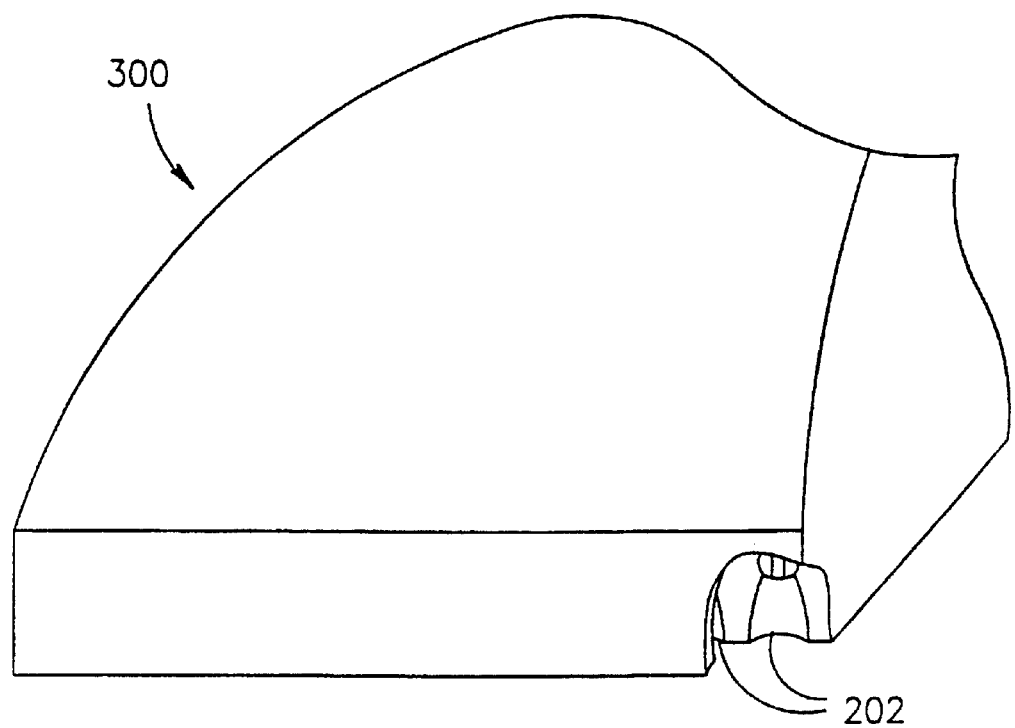
Figure 8:
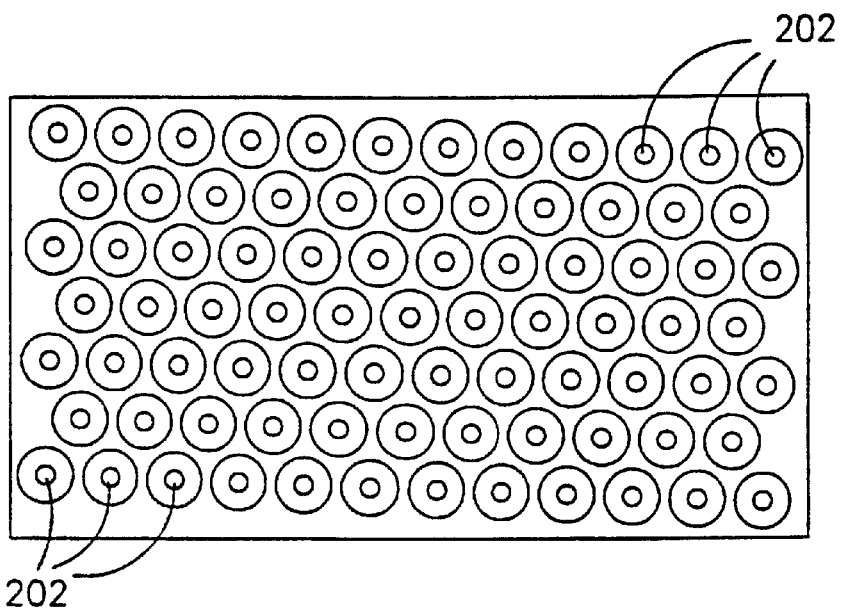

Referring now to FIGS. 7 and 8, there is shown, in accordance with a preferred embodiment of the invention, a multiple nozzle dermabrasion head, referenced generally 300. As seen particularly in FIG. 8, the head 300 includes an array of nozzles, exemplified herein by a plurality of nozzles 202, shown and described above in conjunction with FIGS. 5 and 6. It will be appreciated, however, that this is by way of example only, and head 300 could, for example, alternatively be formed of a similar array of nozzle members 108, shown and described above in conjunction with FIG. 3A.

It is seen that the array of nozzles is arranged so as to provide substantially unbroken coverage over an area considerably larger than that which can be covered by a single nozzle only, thereby to render use of the apparatus of the present invention more efficient. It will be appreciated that the particular array seen in FIG. 8 is by way of example only, and that there may be provided arrays of different sizes, shapes, and configurations, thus providing coverage over areas of various sizes.

It will be appreciated by persons skilled in the art the scope of the present invention is not limited by what has been particularly shown and described above. Rather, the scope of the invention is limited solely by the claims, which follow.

What is claimed is:

1. Apparatus for dermal abrasion, which includes:
    a container for a sterile liquid;
    a fluid delivery head having a liquid entry port and a gas entry port, fluid outlet apparatus, and valve apparatus located between said entry ports and said fluid outlet apparatus and for selectably permitting respective liquid and gas flows from said entry ports to said fluid outlet apparatus;
    liquid conduit apparatus extending between a liquid inlet located within said container and a liquid outlet connected to said liquid entry port of said delivery head;
    gas conduit apparatus extending between a gas inlet and a gas outlet, wherein said gas inlet is connected to a source of pressurized gas and said gas outlet is connected to said gas entry port of said delivery head, and wherein said gas conduit apparatus is connected to said container via an intermediate outlet port; and
    apparatus for selectably exposing said source of sterile liquid to a flow of pressurized gas flowing from said gas inlet to said gas outlet and into said gas entry port of said fluid delivery head, thereby to pump said sterile liquid along said liquid conduit apparatus, from said inlet to said outlet, and into said liquid entry port of said fluid delivery head,
    wherein said fluid outlet apparatus includes at least one gas-liquid combining member arranged to receive said gas and liquid flows and to combine them into a gas-liquid outflow which is operative to exit said fluid outlet apparatus in the form of at least one sterile liquid mist jet suspended in a high velocity gas stream, and wherein each jet is operative, when brought to within a preselected distance from the skin surface to be abraded, to separate therefrom at least a portion of the epidermis,
    and wherein said fluid outlet apparatus defines a fluid outlet port having a predetermined diameter and wherein said preselected distance is not greater than 50 times said predetermined diameter.

2. Apparatus according to claim 1, wherein said gas flow exits said valve apparatus into said gas-liquid combining member at a pressure of a first magnitude, and said combining member is operative to cause a pressure drop in the gas flow therethrough such that the pressure of the gas-liquid outflow downstream of said fluid outlet, is of a second magnitude, wherein said first magnitude is at least twice said second magnitude, so as to cause a shock wave in the gas-liquid flow downstream of said fluid outlet apparatus and atomizing of the liquid portion of said outflow into microscopic droplets, thereby to form a liquid mist suspended in the gas portion of said outflow.

3. Apparatus according to claim 1, wherein said gas inlet of said gas conduit apparatus is constructed for connection to a pressurized gas source, and said gas-liquid outflow is an outflow of said sterile liquid mist suspended in a high velocity air stream.

4. Apparatus according to claim 2, wherein said fluid outlet apparatus also includes apparatus for applying a suction force in the vicinity of the skin surface being abraded so as to remove tissue debris therefrom.

5. Apparatus according to claim 1, wherein said fluid outlet apparatus defines a fluid outlet port having a predetermined diameter and wherein said preselected distance is within the range of 1 to 5 times said predetermined diameter.

6. Apparatus according to claim 1, wherein said at least one nozzle member includes a plurality of nozzles for providing a corresponding plurality of sterile liquid mist jets suspended in high velocity gas streams, and wherein each said jet is operative, when brought to within a preselected distance from the skin surface to be abraded, to separate therefrom at least a portion of the epidermis over a predetermined area.

7. Apparatus according to claim 6, wherein said plurality of nozzles includes an array of nozzles arranged across a predetermined area.

8. Apparatus according to claim 1, wherein said delivery head is configured to be used while being held in one hand.

9. Apparatus according to claim 1, wherein said sterile liquid has suspended therein preselected particles having predetermined abrasive properties.

10. Apparatus according to claim 1, wherein said sterile liquid includes preselected chemical substances operative to cause peeling of predetermined outer layers of the skin.

11. A method of dermal abrasion, which includes:
    exposing a source of sterile liquid to a flow of pressurized gas, thereby to cause a pumped supply thereof into a fluid delivery head;
    supplying the pressurized gas to the fluid delivery head;
    combining the gas and liquid supplied to the fluid delivery head, wherein the fluid delivery head has a fluid outlet with a predetermined internal diameter, so as to provide a gas-liquid outflow in the form of a sterile liquid mist jet suspended in a high velocity gas stream; and
    exposing to the mist jet, at a preselected distance from the fluid outlet, a portion of skin surface sought to be abraded, thereby separating therefrom at least a portion of the epidermis and removing therefrom the resulting tissue debris.

12. A method according to claim 11, wherein the step of supplying the pressurized gas includes supplying the gas at a pressure of a first magnitude, and said step of combining includes causing a pressure drop in the gas flow such that the pressure of the gas-liquid outflow, is of a second magnitude, wherein said first magnitude is at least twice said second magnitude, so as to cause a shock wave in the gas-liquid outflow and atomizing of the liquid portion of the outflow into microscopic droplets, thereby to form a liquid mist suspended in the gas portion of the outflow.

13. A method according to claim 11, and further including the steps, prior to said step of combining, of:
    providing a gas outflow;
    causing an expansion of the gas outflow, thereby to cause, a reduction in the pressure thereof to sub-atmospheric pressure, thereby to provide a suction force; and
    providing a liquid outflow in conjunction with said expanded gas outflow.

14. A method according to claim 12, wherein the gas-liquid outflow has a velocity which is at least a sonic velocity.

15. A method according to claim 11, wherein the pressurized gas is air.

16. A method according to claim 11, wherein the predetermined distance is no greater than 50 times the internal diameter of the fluid outlet.

17. A method according to claim 11, wherein the predetermined distance is within the range of 1–5 times the an internal diameter of the fluid outlet.

18. A method according to claim 11, wherein said step of combining includes the step of providing said liquid mist jet at a pressure in the range of 3–10 atmospheres.

19. A method according to claim 11, wherein said step of combining includes the step of providing said liquid mist jet at a pressure in the range of 3–8 atmospheres.

20. A method according to step 11 wherein the sterile liquid has suspended therein preselected particles having predetermined abrasive properties.

21. A method according to step 11 wherein the sterile liquid includes preselected chemical substances operative to cause peeling of predetermined outer layers of the skin surface.

22. Apparatus for dermal abrasion, which includes:
    a container for a sterile liquid;
    a fluid delivery head having a liquid entry port and a gas entry port, fluid outlet apparatus, and valve apparatus located between said entry ports and said fluid outlet apparatus and for selectably permitting respective liquid and gas flows from said entry ports to said fluid outlet apparatus;
    liquid conduit apparatus extending between a liquid inlet located within said container and a liquid outlet connected to said liquid entry port of said delivery head;
    gas conduit apparatus extending between a gas inlet and a gas outlet, wherein said gas inlet is connected to a source of pressurized gas and said gas outlet is connected to said gas entry port of said delivery head, and wherein said gas conduit apparatus is connected to said container via an intermediate outlet port; and
    apparatus for selectably exposing said source of sterile liquid to a flow of pressurized gas flowing from said gas inlet to said gas outlet and into said gas entry port of said fluid delivery head, thereby to pump said sterile liquid along said liquid conduit apparatus, from said inlet to said outlet, and into said liquid entry port of said fluid delivery head,
    wherein said fluid outlet apparatus includes at least one gas-liquid combining member arranged to receive said gas and liquid flows and to combine them into a gas-liquid outflow which is operative to exit said fluid outlet apparatus in the form of at least one sterile liquid mist jet suspended in a high velocity gas stream, and wherein each jet is operative, when brought to within a preselected distance from the skin surface to be abraded, to separate therefrom at least a portion of the epidermis,
    and wherein said fluid outlet apparatus defines a fluid outlet port having a predetermined diameter and wherein said preselected distance is not greater than 50 times said predetermined diameter
    wherein said gas flow exits said valve apparatus into said gas-liquid combining member at a pressure of a first magnitude and said combining member is operative to cause a pressure drop in the gas flow therethrough such that the pressure of the gas-liquid outflow downstream of said fluid outlet is of a second magnitude, wherein said first magnitude is at least twice said second magnitude so as to cause a shock wave in the gas-liquid flow downstream of said fluid outlet apparatus and atomizing of the liquid portion of said outflow into microscopic droplets thereby to form a liquid mist suspended in the gas portion of said outflow,
    and wherein said fluid outlet apparatus further includes at least one interior nozzle member arranged to provide an outflow of sterile liquid and each said interior nozzle member includes:
    a rear portion configured to fit over said interior nozzle member and arranged to fit over said interior nozzle member so as to define a passageway therebetween for gas flow;
    a waist portion defined by a forward tapering of said rear portion;
    a front portion defining an opening and tapering rearwardly towards said waist portion,
    wherein said passage way is formed so as to be increasingly constricted towards said front portion of said nozzle member, such that said gas flow passing through said passageway is accelerated to at least sonic velocity,
    and wherein said front portion widens toward said opening thereof such that said accelerated gas flow expands and thus undergoes a drop in pressure to a pressure which is sub-atmospheric, such that when said nozzle opening is brought to within a preselected distance from the skin surface to be abraded, at least a portion of the epidermis is separated from the skin surface.

23. Apparatus for dermal abrasion, which includes:
    a container for a sterile liquid;
    a fluid delivery head having a liquid entry port and a gas entry port, fluid outlet apparatus, and valve apparatus located between said entry ports and said fluid outlet apparatus and for selectably permitting respective liquid and gas flows from said entry ports to said fluid outlet apparatus;
    liquid conduit apparatus extending between a liquid inlet located within said container and a liquid outlet connected to said liquid entry port of said delivery head;
    gas conduit apparatus extending between a gas inlet and a gas outlet, wherein said gas inlet is connected to a source of pressurized gas and said gas outlet is connected to said gas entry port of said delivery head, and wherein said gas conduit apparatus is connected to said container via an intermediate outlet port; and
    apparatus for selectably exposing said source of sterile liquid to a flow of pressurized gas flowing from said gas inlet to said gas outlet and into said gas entry port of said fluid delivery head, thereby to pump said sterile liquid along said liquid conduit apparatus, from said inlet to said outlet, and into said liquid entry port of said fluid delivery head,
    wherein said fluid outlet apparatus includes at least one gas-liquid combining member arranged to receive said gas and liquid flows and to combine them into a gas-liquid outflow which is operative to exit said fluid outlet apparatus in the form of at least one sterile liquid mist jet suspended in a high velocity gas stream, and wherein each jet is operative, when brought to within a preselected distance from the skin surface to be abraded, to separate therefrom at least a portion of the epidermis,
    wherein said gas flow exits said valve apparatus into said gas-liquid combining member at a pressure of a first magnitude and said combining member is operative to cause a pressure drop in the gas flow therethrough such that the pressure of the gas-liquid outflow downstream of said fluid outlet is of a second magnitude, wherein said first magnitude is at least twice said second magnitude so as to cause a shock wave in the gas-liquid flow downstream of said fluid outlet apparatus and atomizing of the liquid portion of said outflow into microscopic droplets thereby to form a liquid mist suspended in the gas portion of said outflow, and wherein said fluid outlet apparatus defines a fluid outlet port, said fluid outlet apparatus including at least one interior nozzle member having an interior diameter wherein said preselected distance is not greater than 50 times said internal diameter, said interior nozzle member arranged to provide an outflow of sterile liquid, each said interior nozzle member including:

a rear portion configured to fit over said interior nozzle member and arranged to fit over said interior nozzle member so as to define a passageway therebetween for gas flow;

a waist portion defined by a forward tapering of said rear portion;

a front portion defining an opening and tapering rearwardly towards said waist portion, wherein said passage way is formed so as to be increasingly constricted towards said front portion of said nozzle member, such that said gas flow passing through said passageway is accelerated to at least sonic velocity, and wherein said front portion widens toward said opening thereof such that said accelerated gas flow expands and thus undergoes a drop in pressure to a pressure which is sub-atmospheric, such that when said nozzle opening is brought to within a preselected distance from the skin surface to be abraded, at least a portion of the epidermis is separated from the skin surface.

24. Apparatus for dermal abrasion, which includes:

a container for a sterile liquid;

a fluid delivery head having a liquid entry port and a gas entry port, fluid outlet apparatus, and valve apparatus located between said entry ports and said fluid outlet apparatus and for selectably permitting respective liquid and gas flows from said entry ports to said fluid outlet apparatus;

liquid conduit apparatus extending between a liquid inlet located within said container and a liquid outlet connected to said liquid entry port of said delivery head;

gas conduit apparatus extending between a gas inlet and a gas outlet, wherein said gas inlet is connected to a source of pressurized gas and said gas outlet is connected to said gas entry port of said delivery head, and wherein said gas conduit apparatus is connected to said container via an intermediate outlet port; and apparatus for selectably exposing said source of sterile liquid to a flow of pressurized gas flowing from said gas inlet to said gas outlet and into said gas entry port of said fluid delivery head, thereby to pump said sterile liquid along said liquid conduit apparatus, from said inlet to said outlet, and into said liquid entry port of said fluid delivery head, wherein said fluid outlet apparatus includes at least one gas-liquid combining member arranged to receive said gas and liquid flows and to combine them into a gas-liquid outflow which is operative to exit said fluid outlet apparatus in the form of at least one sterile liquid mist jet suspended in a high velocity gas stream, and wherein each jet is operative, when brought to within a preselected distance from the skin surface to be abraded, to separate therefrom at least a portion of the epidermis, wherein said gas flow exits said valve apparatus into said gas-liquid combining member at a pressure of a first magnitude and said combining member is operative to cause a pressure drop in the gas flow therethrough such that the pressure of the gas-liquid outflow downstream of said fluid outlet is of a second magnitude, wherein said first magnitude is at least twice said second magnitude so as to cause a shock wave in the gas-liquid flow downstream of said fluid outlet apparatus and atomizing of the liquid portion of said outflow into microscopic droplets thereby to form a liquid mist suspended in the gas portion of said outflow, and wherein said fluid outlet apparatus defines a fluid outlet port, said fluid outlet apparatus including at least one interior nozzle member having an interior diameter wherein said preselected distance is within a range of 1 to 5 times said internal diameter, said interior nozzle member arranged to provide an outflow of sterile liquid, each said interior nozzle member including:

a rear portion configured to fit over said interior nozzle member and arranged to fit over said interior nozzle member so as to define a passageway therebetween for gas flow;

a waist portion defined by a forward tapering of said rear portion;

a front portion defining an opening and tapering rearwardly towards said waist portion, wherein said passage way is formed so as to be increasingly constricted towards said front portion of said nozzle member, such that said gas flow passing through said passageway is accelerated to at least sonic velocity, and wherein said front portion widens toward said opening thereof such that said accelerated gas flow expands and thus undergoes a drop in pressure to a pressure which is sub-atmospheric, such that when said nozzle opening is brought to within a preselected distance from the skin surface to be abraded, at least a portion of the epidermis is separated from the skin surface.

* * * * *